(12) United States Patent
Gerber et al.

(10) Patent No.: US 10,744,253 B2
(45) Date of Patent: Aug. 18, 2020

(54) ADAPTIVE PERITONEAL DIALYSIS INTRA-SESSION ADJUSTMENTS FOR OVERALL SESSION OPTIMIZATION

(71) Applicant: Medtronic, Inc., Minneapolis, MN (US)

(72) Inventors: Martin T. Gerber, Maple Grove, MN (US); Christopher M. Hobot, Rogers, MN (US)

(73) Assignee: Medtronic, Inc., Minneapolis, MN (US)

( * ) Notice: Subject to any disclaimer, the term of this patent is extended or adjusted under 35 U.S.C. 154(b) by 164 days.

(21) Appl. No.: 15/666,622

(22) Filed: Aug. 2, 2017

(65) Prior Publication Data

US 2018/0043078 A1 Feb. 15, 2018

Related U.S. Application Data

(60) Provisional application No. 62/373,050, filed on Aug. 10, 2016.

(51) Int. Cl.
*A61M 1/28* (2006.01)
*A61M 1/16* (2006.01)

(52) U.S. Cl.
CPC .......... *A61M 1/282* (2014.02); *A61M 1/1613* (2014.02); *A61M 1/1696* (2013.01);
(Continued)

(58) Field of Classification Search
CPC .... A61M 1/282; A61M 1/1613; A61M 1/287; A61M 1/28; A61M 1/1696;
(Continued)

(56) References Cited

U.S. PATENT DOCUMENTS 4,747,822 A 5/1988 Peabody
4,976,683 A 12/1990 Gauthier
(Continued)

FOREIGN PATENT DOCUMENTS

CN 105008893 B 10/2015
DE 3224823 1/1984
(Continued)

OTHER PUBLICATIONS

European Search Report for App. No. 17185808.7, dated Jan. 2, 2018.
(Continued)

*Primary Examiner* — Amber R Stiles
(74) *Attorney, Agent, or Firm* — Hahn & Associates

(57) ABSTRACT

The invention relates to systems and methods for adjusting one or more dialysis parameters for delivering a peritoneal dialysis cycle to a patient based on patient or system parameters. The systems and methods include various sensors, flow paths, and processors to adjust the dialysis parameters used to deliver peritoneal dialysis therapy, for a specific peritoneal dialysis cycle. For example, a first peritoneal dialysis cycle can provide data on patient or system parameters that can be used to adjust the dialysis parameters used to deliver a subsequent peritoneal dialysis cycle. One or more peritoneal dialysis cycles are contained in a particular peritoneal dialysis therapy session. Patient parameters can include patient blood pressure; volume of fluid removed; patient goal; blood solute level; effluent solute level; effluent temperature; effluent color or clarity; patient posture; tidal volume remaining in patient; and intraperitoneal pressure.

19 Claims, 4 Drawing Sheets

(52) U.S. Cl.
CPC ............. *A61M 1/28* (2013.01); *A61M 1/287* (2013.01); *A61M 2205/3303* (2013.01); *A61M 2205/3306* (2013.01); *A61M 2205/3317* (2013.01); *A61M 2205/3344* (2013.01); *A61M 2205/3368* (2013.01); *A61M 2205/3386* (2013.01); *A61M 2205/50* (2013.01); *A61M 2205/52* (2013.01); *A61M 2230/005* (2013.01); *A61M 2230/30* (2013.01); *A61M 2230/50* (2013.01); *A61M 2230/62* (2013.01)

(58) Field of Classification Search
CPC ........ A61M 2230/50; A61M 2230/005; A61M 2205/3306; A61M 2205/3303; A61M 2230/30; A61M 2205/3317; A61M 2205/3344; A61M 2205/3368; A61M 2205/3386; A61M 2205/50; A61M 2205/52; A61M 2230/62
See application file for complete search history.

(56) References Cited

U.S. PATENT DOCUMENTS

| | | | |
|---|---|---|---|
| 5,032,265 | A | 7/1991 | Jha |
| 5,141,493 | A | 8/1992 | Jacobsen |
| 5,643,201 | A | 7/1997 | Peabody |
| 2004/0019320 | A1* | 1/2004 | Childers ............... A61M 1/28 604/29 |
| 2008/0200866 | A1 | 8/2008 | Prisco |
| 2009/0149776 | A1 | 6/2009 | Adams |
| 2010/0010425 | A1 | 1/2010 | Yu |
| 2010/0137782 | A1 | 6/2010 | Jansson |
| 2010/0312172 | A1 | 12/2010 | Hoffman |
| 2012/0029937 | A1 | 2/2012 | Neftel |
| 2012/0135396 | A1 | 5/2012 | McDevitt |
| 2012/0273354 | A1* | 11/2012 | Orhan .................... A61M 1/28 204/519 |
| 2012/0277551 | A1 | 11/2012 | Gerber |
| 2013/0186759 | A1 | 7/2013 | Lin |
| 2014/0018727 | A1 | 1/2014 | Burbank |
| 2014/0216250 | A1 | 8/2014 | Meyer |
| 2015/0148697 | A1 | 5/2015 | Burnes |
| 2016/0143774 | A1 | 5/2016 | Burnett |

FOREIGN PATENT DOCUMENTS

| | | |
|---|---|---|
| EP | 0402505 | 12/1990 |
| WO | WO1999006082 | 2/1999 |
| WO | WO2000057935 A1 | 10/2000 |
| WO | WO20020053211 | 7/2002 |
| WO | WO2009094035 A1 | 1/2008 |
| WO | 20090154955 | 12/2009 |
| WO | WO2009154955 A2 | 12/2009 |
| WO | WO 20100002830 | 1/2010 |
| WO | WO2014121161 | 8/2014 |
| WO | WO 20140121169 | 8/2014 |
| WO | WO 20150130205 | 9/2015 |
| WO | WO 20160080883 | 5/2016 |
| WO | WO 20170034452 | 3/2017 |

OTHER PUBLICATIONS

European Search Report for App. No. 17185638.8, dated Dec. 19, 2017.
European Search Report for App. No. 17185810.3, dated Dec. 15, 2017.
European Search Report for App. No. 17185636.2, dated Mar. 27, 2018.
PCTUS20170146199 ISR and written opinion, dated Feb. 19, 2018.
European Search Report for App. No. 17185636.2 dated Jan. 10, 2018.
PCTUS2017025858 International Search Report dated Jun. 29, 2017.
PCTUS2017025858 Written Opinion dated Jun. 29, 2017.
PCT/US2017/025868 International Search Report dated Jun. 29, 2017.
PCT/US2017/025868 Written Opinion dated Jun. 29, 2017.
PCTUS2017025876 International Search Report dated Jun. 29, 2017.
PCTUS2017025876 Written Opinion dated Jun. 29, 2017.
Office Action for European Application No. 17185636.2, dated Mar. 19, 2020.

\* cited by examiner

ADAPTIVE PERITONEAL DIALYSIS INTRA-SESSION ADJUSTMENTS FOR OVERALL SESSION OPTIMIZATION

CROSS-REFERENCE TO RELATED APPLICATIONS

This application claims the benefit of and priority to U.S. Provisional Patent Application No. 62/373,050 filed Aug. 10, 2016, the entire disclosure of which is incorporated by reference herein.

FIELD OF THE INVENTION

The invention relates to systems and methods for adjusting one or more dialysis parameters for delivering a peritoneal dialysis cycle to a patient based on patient or system parameters. The systems and methods include various sensors, flow paths, and processors to adjust the dialysis parameters used to deliver peritoneal dialysis therapy, for a specific peritoneal dialysis cycle. For example, a first peritoneal dialysis cycle can provide data on patient or system parameters that can be used to adjust the dialysis parameters used to deliver a subsequent peritoneal dialysis cycle. One or more peritoneal dialysis cycles are contained in a particular peritoneal dialysis therapy session.

BACKGROUND

Peritoneal Dialysis (PD) is a dialysis treatment that differs from Hemodialysis (HD) because blood is not removed from the body and passed through a dialyzer, but a catheter is placed in the peritoneal cavity and peritoneal dialysis fluid is cycled into and out of the peritoneal cavity to accomplish dialysis. Blood is cleaned inside the patient using the patient's own peritoneum as a type of dialysis membrane. The two primary classes of PD are Continuous Ambulatory Peritoneal Dialysis (CAPD) and Continuous Cycling Peritoneal Dialysis (CCPD) (or Automated Peritoneal Dialysis (APD)). In CAPD, dialysis is performed continuously by positioning a bag of peritoneal dialysate at shoulder level and using gravity to introduce the fluid into the peritoneal cavity. After a period of time the used dialysate is then drained from the cavity and discarded. The time period that the dialysate is in the cavity is called the dwell time and can range from 30 minutes to 4 hours or more. CAPD is typically performed three, four or five times in a 24-hour period while a patient is awake. CAPD requires no cycler to deliver and remove the fluid.

Continuous Cycling Peritoneal Dialysis (CCPD) or Automated Peritoneal Dialysis (APD) uses a machine called a cycler to fill and empty the peritoneal cavity multiple times during a particular therapy session. The machine (cycler) delivers and then drains the peritoneal dialysate. Typically, CCPD is performed at night while the patient is asleep. In some cases, a patient may require a combination of CAPD and CCPD to receive an appropriate treatment. For example, some patients use a cycler at night for CCPD but also perform one or more manual CAPD exchanges during the day.

The effectiveness of CCPD can depend on several factors, unique to specific patients. The factors, including the number of cycles in a session, the dwell time of a cycle, the volume of a cycle, and the composition of the peritoneal dialysate, can influence patient comfort and therapy effectiveness. Further, changes to the patient during a cycle can result in less effective therapy from subsequent cycles within the same peritoneal dialysis session. Yet, known CCPD systems do not provide any mechanism to make changes to peritoneal dialysis cycles within a peritoneal dialysis session based on the changing needs of a patient during a single therapy session. Rather, known CPPD are restricted to automatically functioning based on pre-programmed settings without adjustment from cycle to cycle. Importantly, the known systems must rely on set pre-programmed settings because the known systems and methods lack the capability to create or adjust peritoneal dialysate based on newly received data.

Hence, there is a need for systems and methods that can modify one or more patient or dialysis machine parameters from cycle-to-cycle, or "intra-session," within a therapy session to optimize peritoneal dialysis therapy and patient comfort. There is also a need for systems and methods to generate peritoneal dialysate in accordance with any adjusted dialysate prescription. The need includes optimizing multiple cycles or exchanges over a dialysis therapy session and requires the use of systems and methods capable of creating or adjusting a peritoneal dialysate.

SUMMARY OF THE INVENTION

The first aspect of the invention relates to a computer implemented method of adjusting intercycle patient parameters during peritoneal dialysis therapy. In any embodiment, the method can include receiving one or more patient physiological parameters during a peritoneal dialysis session; receiving one or more dialysis parameters used during the peritoneal dialysis session; storing the one or more patient parameters and one or more dialysis parameters in a machine-readable storage medium for storing instructions, which when executed by a dialysis machine performs the step of adjusting one or more dialysis parameters for a subsequent cycle of the peritoneal dialysis session based on the patient parameters and dialysis parameters.

In any embodiment, the one or more patient parameters can include any one of patient blood pressure; volume of fluid removed; patient goal; blood solute level; effluent solute level; effluent temperature; effluent color or clarity; patient posture; tidal volume remaining in patient; intraperitoneal pressure; and combinations thereof.

In any embodiment, the step of adjusting one or more dialysis parameters can include adjusting any one of number of cycles; dwell time; dialysate temperature; fill volume; dialysate pH; dialysate osmotic agent concentration; fluid removal volume; drain volume; fill rate; drain rate; and combinations thereof.

In any embodiment, the step of receiving one or more patient physiological parameters during a peritoneal dialysis session can include sampling a peritoneal dialysate effluent.

In any embodiment, at least one patient physiological parameter can be obtained from a sensor positioned in an integrated cycler.

In any embodiment, at least one patient physiological parameter can be obtained from an implantable or wearable sensor.

In any embodiment, the method can include the steps of receiving a target fluid removal volume; comparing the volume of effluent removed to the target fluid removal volume; and the step of adjusting one or more dialysis parameters for a subsequent cycle can include the step of adjusting the dialysate osmotic agent concentration.

In any embodiment, the step of adjusting the dialysate osmotic agent concentration can include increasing an osmotic agent concentration if the target fluid removal volume is higher than the volume of effluent removed; and decreasing the osmotic agent concentration if the target fluid removal volume is lower than the volume of effluent removed.

In any embodiment, the method can include receiving a target fluid removal volume; comparing the volume of effluent removed to the target fluid removal volume; and the step of adjusting one or more dialysis parameters for a subsequent cycle can include the step of adjusting the dwell time, the number of cycles, or combinations thereof.

In any embodiment, wherein the step of adjusting one or more dialysis parameters can be carried out by a processor in communication with a peritoneal dialysate generation flow path.

In any embodiment, the method can include the steps of determining a change in patient blood pressure during the peritoneal dialysis cycle; and decreasing the dialysate osmotic agent concentration in a subsequent cycle if the change in patient blood pressure exceeds a predetermined threshold.

In any embodiment, the patient goal can be any one of an expected fluid intake, an expected diet, an expected dialysis schedule, and combinations thereof; and the step of adjusting one or more dialysis parameters for a subsequent cycle of the peritoneal dialysis session can include increasing an osmotic agent concentration in response to a high expected fluid intake, a high salt diet, an expected dialysis schedule of fewer dialysis sessions, and combinations thereof.

In any embodiment, the method can include the step of adjusting a temperature of peritoneal dialysate for a subsequent session to be within a predetermined range of the effluent temperature.

In any embodiment, the step of adjusting the one or more dialysis parameters for a subsequent cycle can include increasing the dwell time, the osmotic agent concentration, or combinations thereof if the patient posture is determined to be erect.

In any embodiment, the method can include the step of obtaining an intra-session history for a patient; and wherein the peritoneal dialysate prescription is adjusted based on the intra-session history for a patient.

The features disclosed as being part of the first aspect of the invention can be in the first aspect of the invention, either alone or in combination.

The second aspect of the invention is drawn to a system for adjusting intercycle patient parameters during peritoneal dialysis. In any embodiment, the system can include a peritoneal dialysate generation flow path having (i) a water source fluidly connectable to the peritoneal dialysate generation flow path; (ii) one or more water purification modules fluidly connectable to the peritoneal dialysate generation flow path; (iii) one or more concentrate sources fluidly connectable to the peritoneal dialysate generation flow path; the concentrate source containing one or more solutes and including at least an osmotic agent source and an ion concentrate source; (iv) at least one concentrate pump; the concentrate pump controlling the movement of fluid from the concentrate sources to the peritoneal dialysate generation flow path; (v) a sterilization module fluidly connectable to the peritoneal dialysate generation flow path; an integrated cycler fluidly connected to the peritoneal dialysate generation flow path; the integrated cycler having at least an infusion line and an effluent line or a combined infusion and effluent line; and a processor; the processor determining a peritoneal dialysate prescription and controlling the concentrate pump and integrated cycler based on a peritoneal dialysate prescription.

In any embodiment, the processor can have one or more input/output interfaces for receiving one or more patient parameters.

In any embodiment, the system can have a peritoneal dialysate regeneration module fluidly connected to the effluent line or combined infusion and effluent line and the peritoneal dialysate generation flow path.

In any embodiment, the processor can perform the method of the first aspect of the invention.

In any embodiment, the system can include at least one sensor positioned in the effluent line or combined infusion and effluent line and in communication with the processor.

In any embodiment, the sensor can sense any one of a temperature of a fluid in the effluent line or combined infusion and effluent line; a conductivity of the fluid in the effluent line or combined infusion and effluent line; an ion concentration of the fluid in the effluent line or combined infusion and effluent line; or combinations thereof.

The features disclosed as being part of the second aspect of the invention can be in the second aspect of the invention, either alone or in combination.

DETAILED DESCRIPTION OF THE INVENTION

Figure 1:
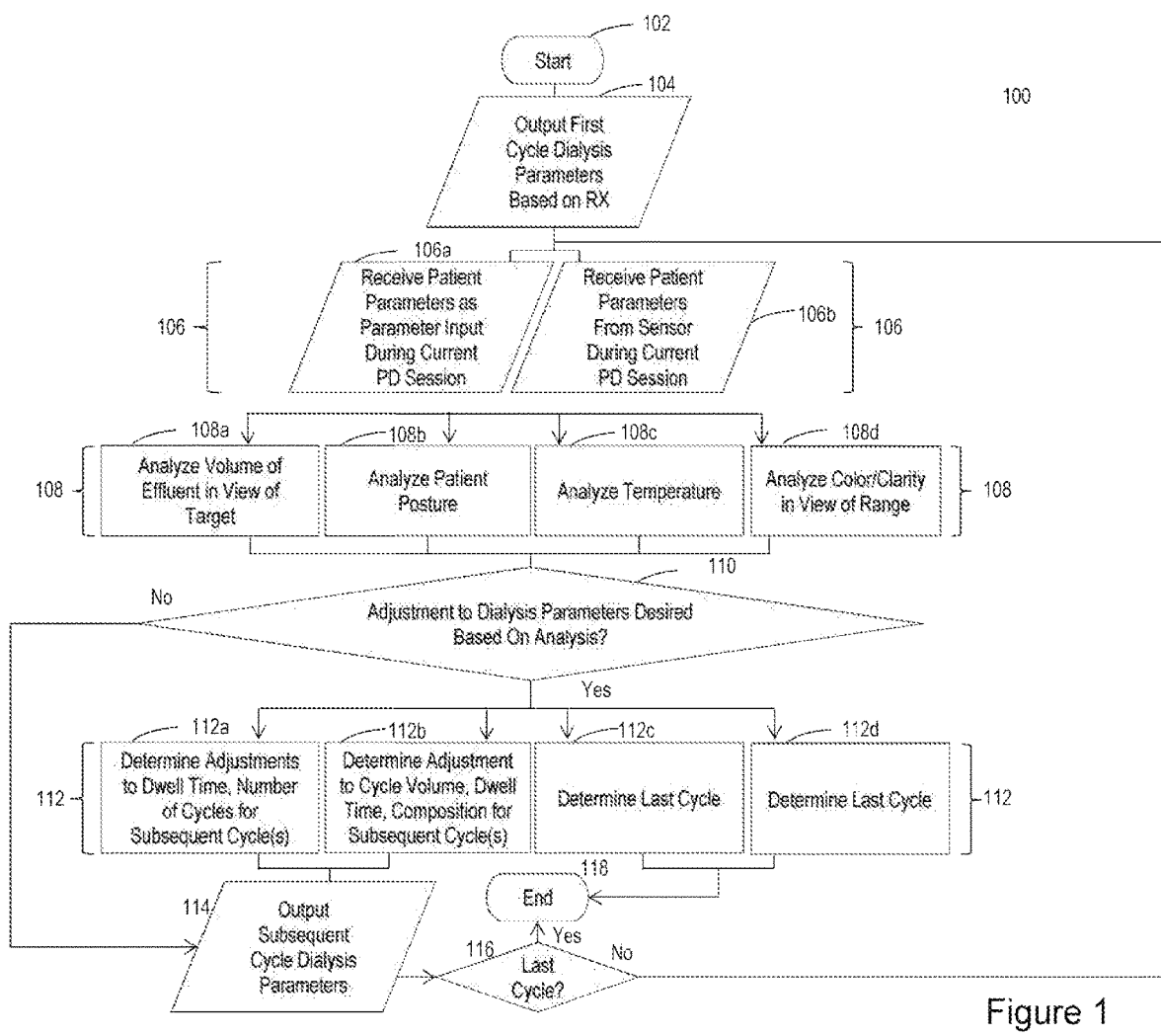
FIG. 1 shows a flow chart for a method of adjusting subsequent cycle dialysate parameters based on patient parameters received during a prior cycle.

Unless defined otherwise, all technical and scientific terms used generally have the same meaning as commonly understood by one of ordinary skill in the art.

The articles "a" and "an" are used to refer to one or to over one (i.e., to at least one) of the grammatical object of the article. For example, "an element" means one element or over one element.

The term "adjusting" or to "adjust" a dialysis parameter refers to changing any parameter of a peritoneal dialysis session, including changing the concentration of one or more solutes, the temperature, the dwell time, and the number of cycles.

The term "blood solute level" refers to the concentration of a solute in the blood of a patient.

The term "change in patient blood pressure" refers to a difference in the blood pressure of a patient as measured at two different times.

The term "communication" refers to an electronic or wireless link between two components.

The term "comparing" or to "compare" refers to determining the differences, if any, between two values or parameters.

The term "comprising" includes, but is not limited to, whatever follows the word "comprising." Use of the term indicates the listed elements are required or mandatory but that other elements are optional and may be present.

The term "computer implemented" refers to a process or set of steps carried out by a processor, computer, or any other electronic system.

The term "concentrate pump" refers to a pump positioned to control the movement of fluid between a concentrate source and a peritoneal dialysate generation flow path.

A "concentrate source" is a source of one or more solutes. The concentrate source can have one or more solutes with a solute concentration greater than the solute concentration to be used for dialysis. The concentrate in the concentrate source can also be lower than the solute concentration generally used in dialysis for generation of low concentration dialysate.

The terms "concentration" and "solute concentration" refers to an amount of a solute dissolved in a given amount of a solvent.

The term "conductivity" refers to the inverse of the electrical resistance of a fluid.

The term "consisting of" includes and is limited to whatever follows the phrase "consisting of" The phrase indicates the limited elements are required or mandatory and that no other elements may be present.

The term "consisting essentially of" includes whatever follows the term "consisting essentially of" and additional elements, structures, acts or features that do not affect the basic operation of the apparatus, structure or method.

The terms "control," "controlling," or "controls" refers to the ability of one component to direct the actions of a second component.

The phrase "controlling the movement of fluid" refers to directing fluid through a flow path, container, receptacle, or reservoir of any type.

The term "cycle" or "peritoneal dialysis cycle" refers to the infusion of peritoneal dialysate into a patient, a dwell of the peritoneal dialysate within the peritoneal cavity of the patient, and the removal of the peritoneal dialysate from the peritoneal cavity of the patient. The process of filling and then draining your abdomen can also be seen as an "exchange" of used and clean fluids. However, the number, length, and timing of "cycles" or "exchanges" are non-limiting. For example, Continuous Ambulatory Peritoneal Dialysis (CAPD) and Continuous Cycling Peritoneal Dialysis (CCPD) may occur on different schedules, but the process of filling and then draining the peritoneal cavity can be referred to as "cycles" for both CAPD and CCPD. As such, the term is "cycle" or exchange refers to any particular dialysis schedule or type of dialysis.

A "dialysis parameter" is any factor of a peritoneal dialysis session that can affect the health of a patient during and after dialysis. The term "dialysis parameter" includes, but is not limited to, occurrence of dialysis, fluid removal in a cycle, fluid removal rate, concentration of one or more solutes in a peritoneal dialysate, a number of cycles in a peritoneal dialysis session, a dwell time of a cycle, temperature of the peritoneal dialysate, or any other factor used in peritoneal dialysis.

The terms "determining" and "determine" refer to ascertaining a particular state of a system or variable(s).

The term "dialysate osmotic agent concentration" or "osmotic agent concentration" refers to the amount of an osmotic agent per unit volume of peritoneal dialysate.

The term "dialysate pH" refers to the concentration of hydrogen ions in a dialysate to be infused into a patient.

The term "dialysate temperature" refers to the temperature of a peritoneal dialysate to be infused into a patient.

The term "drain rate" refers to a volume, quantity, or amount of fluid removed from the peritoneal cavity of a patient per unit time.

The term "drain volume" refers to a volume, quantity, or amount of fluid removed from the peritoneal cavity of a patient at the end of a cycle.

The term "dwell time" refers to the amount of time elapsed between infusion of peritoneal dialysate into a patient and drainage of the peritoneal dialysate out of the patient.

The term "erect" refers to a posture of a patient standing, or sitting up as opposed to supine.

The term "effluent" or "peritoneal dialysate effluent" refers to fluid removed from the peritoneal cavity of a patient during peritoneal dialysis therapy.

The term "effluent clarity" refers to the percentage of light shined on a fluid removed from the peritoneal cavity of a patient that passes through the fluid.

The term "effluent color" refers to the wavelength(s) of light absorbed or transmitted by a fluid removed from the peritoneal cavity of a patient.

The term "effluent line" refers to a fluid connector for removing fluid from a peritoneal cavity of a patient. The term effluent line can also refer to a combined infusion and effluent line.

The term "effluent solute level" refers to the concentration of a solute in effluent removed from the peritoneal cavity of a patient.

The term "effluent temperature" refers to the temperature of fluid removed from the peritoneal cavity of a patient.

The term "execute" means to carry out a process or series of steps.

The term "expected dialysis schedule" refers to the timing of peritoneal dialysis sessions or cycles a patient expects to receive or desires to receive in the future.

The term "expected diet" refers to the type and amount of food that a patient believes will be ingested in a given time period.

The term "expected fluid intake" refers to a volume of fluid that a patient believes will be ingested in a given time period.

A "fluid" is a liquid substance optionally having a combination of gas and liquid phases in the fluid. Notably, a liquid can therefore also have a mixture of gas and liquid phases of matter.

The term "fluid removal volume" refers to a volume of fluid removed from a patient during a peritoneal dialysis cycle. The fluid removal volume can refer to the net fluid removal volume, which is equal to the difference between the amount of peritoneal dialysate infused into the patient and the amount of effluent removed from the patient with full draining. The term "fluid removal volume" can also refer to any amount of fluid removed from the patient.

The terms "fluidly connectable," "fluidly connected," "fluid connection" "fluidly connectable," or "fluidly connected" refer to the ability to pass fluid, gas, or mixtures thereof from one point to another point. The two points can be within or between any one or more of compartments, modules, systems, and components, all of any type.

The term "high expected fluid intake" refers to an expected fluid intake that is higher than an average for a patient.

The term "high salt diet" refers to food with an amount of sodium higher than the average diet for a patient.

The term "implantable sensor" describes a device, component or module intended to be totally or partially introduced, surgically or medically into a mammalian body, or by medical intervention that remains after the procedure and can sense one or more patient physiological parameters.

An "infusion line" is a fluid line for carrying peritoneal dialysate into a body cavity or part of a patient such as a peritoneal cavity. The term infusion line can also refer to a combined infusion and effluent line.

The term "input/output interface" refers to a module of a processor or computing system that allows data to be received by the processor or computing system and provided by the processor or computing system. The input/output interfaces can automatically receive and provide data from sensors, or can receive data manually input through the interface, such as by a keyboard.

The term "instructions" refers to digital information that, when read or executed by a computer, processor, or system, cause the computer, processor, or system to carry out a series of steps.

An "integrated cycler" is a component for movement of fluid into and out of the peritoneal cavity of a patient, wherein the integrated cycler forms a part of an overall system. For example, the integrated cycler can be contained in a housing with other components used for peritoneal dialysis and be in fluid and electrical connection with desired components.

The term "intercycle" refers to changes made to dialysis parameters between multiple cycles of a dialysis session.

The term "intraperitoneal pressure" refers to the fluid pressure within the peritoneal cavity of a patient.

The term "intra-session history" refers to the dialysis parameters used and the resulting patient parameters or dialysis results from one or more cycles, including previous cycles, in an ongoing peritoneal dialysis session.

An "ion concentrate source" refers to a source of one or more ionic compounds. The ion concentrate source can be in water or solid form. The ion concentrate source can further have one or more ionic compounds that are at a higher ion concentration greater than generally used in dialysis. In other words, an ion concentration for each particular ion can be adjusted. The concentration of the ionic compounds in the ion concentrate source can also be lower than the concentration generally used in dialysis for generation of low concentration dialysate.

The term "machine-readable storage medium" refers to any electronic device capable of storing information in a digital format for reading by a computer, processor, or other electronic device.

The term "number of cycles" refers to the number of times peritoneal dialysate is infused into and drained from a patient in a given peritoneal dialysis session.

An "osmotic agent source" refers to a source of osmotic agents in solid and/or solution form. The osmotic agent source can interface with at least one other module found in systems for dialysis. The osmotic agent source can contain at least one fluid pathway and include components such as conduits, valves, filters or fluid connection ports, any of which are fluidly connectable to each other or to a fluid flow path. The osmotic agent source can either be formed as a stand-alone enclosure or a compartment integrally formed with an apparatus for dialysis for containing an osmotic agent source. The osmotic agent concentration in the osmotic agent source can be lower or higher than the osmotic agent concentration generally used in dialysis for generation of low or high osmotic agent concentration dialysate.

A "patient" or "subject" is a member of any animal species, preferably a mammalian species, optionally a human. The subject can be an apparently healthy individual, an individual suffering from a disease, or an individual being treated for a disease.

The term "patient blood pressure" or "blood pressure" refers to the pressure of blood in the body of a patient and can refer to systolic pressure, diastolic pressure, or a combination thereof.

The term "patient goal" refers to a desired peritoneal dialysis schedule, outcome, or any desired patient lifestyle factors. The patient goal can refer to an expected or desired schedule, diet, exercise, or any other patient factors.

The term "patient parameter" refers to any data without limitations that gives any medical relevant information about the health status of a patient. A patient physiological parameter can include, but is not limited to, blood pressure, blood solute levels, posture or any other medically relevant information. For example, the physiological parameters can encompasses information such as age, weight, gender, current drug therapies, smoking habits, diet, etc.

The term "patient posture" refers to a position of the patient's body during therapy, such as sitting, standing, or lying down.

The term "peritoneal cavity" refers to a space between the parietal peritoneum and visceral peritoneum of a patient.

"Peritoneal dialysate" is a dialysis solution to be used in peritoneal dialysis having specified parameters for purity and sterility. Peritoneal dialysate is different than the dialysate used in hemodialysis, although peritoneal dialysate may be used in hemodialysis.

A "peritoneal dialysate generation flow path" is a path used in generating dialysate suitable for peritoneal dialysis.

A "peritoneal dialysate prescription" refers to the set parameters of a peritoneal dialysis session or cycle, including the concentration of one or more solutes in the dialysate, the temperature, the dwell time, and the number of cycles in a session.

The term "peritoneal dialysate regeneration module" refers to a component or components capable of removing waste products from a fluid.

"Peritoneal dialysis" is a therapy wherein a dialysate is infused into the peritoneal cavity, which serves as a natural dialyzer. In general, waste components diffuse from a patient's bloodstream across a peritoneal membrane into the dialysis solution via a concentration gradient. In general, excess fluid in the form of plasma water flows from a patient's bloodstream across a peritoneal membrane into the dialysis solution via an osmotic gradient. Once the infused peritoneal dialysis solution has captured sufficient amounts of the waste components the fluid is removed. The cycle can be repeated for several cycles each day or as needed.

A "peritoneal dialysis session" is a set of peritoneal dialysis cycles performed over a time period as part of ongoing therapy. The peritoneal dialysis session can last a day or more, and can include any number of cycles.

The term "positioned" refers to the location of a component.

The term "predetermined range" is a range of possible values for a parameter to be set as.

The term "predetermined threshold" refers to a value for a parameter, set before analysis to which the analyzed parameter can be compared. Whether the analyzed parameter exceeds or does not exceed the predetermined threshold can direct or cause some action to be taken.

The term "processor" is a broad term and is to be given its ordinary and customary meaning to a person of ordinary skill in the art. The term refers without limitation to a computer system, state machine, and/or processor designed to perform arithmetic or logic operations using logic circuitry that responds to and processes the basic instructions that drive a computer. In any embodiment of the first, second, third, and fourth invention, the terms can include ROM ("read-only memory") and/or RAM ("random-access memory") associated therewith.

The term "pump" refers to any device that causes the movement of fluids or gases by applying suction or pressure.

The term "receiving" or to "receive" means to obtain information from any source.

The term "sampling" or "to sample" refers to sensing one or more characteristics of a fluid with a sensor.

The term "sensing" or to "sense" refers to determining one or more states of one or more variables in a system.

A "sensor" is a component capable of determining one or more states of one or more variables in a system.

A "solute" is a substance dissolved in, or intended to be dissolved in, a solvent.

A "sterilization module" is a component or set of components to sterilize a fluid by removing or destroying chemical or biological contaminants.

The term "storing" or to "store" refers to saving electronic data or information in a machine readable medium.

The term "subsequent cycle" refers to a cycle in a peritoneal dialysis session occurring after a present or ongoing cycle.

The term "target fluid removal volume" is a net or given fluid removal volume from a peritoneal dialysis session that is expected or desired.

The term "tidal volume remaining in a patient" refers to a volume of fluid from one peritoneal dialysis cycle that is not removed from the peritoneal cavity of the patient at the end of the cycle.

The term "water purification module" refers to a component or components capable of removing biological or chemical contaminants from water.

The term "water source" refers to a source from which potable water can be obtained.

A "wearable sensor" is a sensor capable of detecting one or more patient parameters from contact with the skin of the patient. The wearable sensor is external to the patient, but in contact with the patient such as a patch adhered to a skin surface of the patient.

Adaptive Peritoneal Intra-Session Adjustments

FIG. 1 is a flowchart of a computer implemented method 100 for monitoring patient parameters during a peritoneal dialysis session to adjust dialysis parameters for a subsequent cycle within the same peritoneal dialysis session. The method can be performed using a system programmed or constructed to monitor patient parameters during a peritoneal dialysis session and to make intercycle modifications within the same peritoneal dialysis session. The system can include a machine readable storage medium including instructions that, when executed by a dialysis machine, cause the dialysis machine and related components to perform the described methods.

The method 100 can begin in operation 102. A peritoneal dialysis session can be initiated. In operation 104, control signals implementing dialysis parameters for a first cycle can be sent to components of the system based on a peritoneal dialysis prescription. For example, a processor of the system can be in communication with a concentrate source of the system and can control the movement of fluid from the concentrate source to a peritoneal dialysate generation flow path of the system based on the dialysis parameters for the first cycle of the peritoneal dialysis session. One of skill in the art will understand that the methods are not limited to the first cycle of a peritoneal dialysis session, and can be used in the second, third, or later cycle of a peritoneal dialysis session. If a patient receives a combination therapy of CAPD and CCPD, the processor can generate a peritoneal dialysate based on the dialysis parameters received from a prior CAPD session for delivering an appropriate dialysis dose during a first cycle of CCPD.

In operation 106, one or more patient parameters can be received during or after the current cycle of the peritoneal dialysis session and stored in a machine-readable storage medium. Patient parameters can be received as parameter input into a computing device of the system and/or from the one or more sensors of the system. For example, a patient posture (laying down, sitting up, or erect) can be entered manually into the system and received into the computing device as parameter input. Alternatively, an implanted accelerometer can determine patient posture and the patient posture can be transmitted to the processor through wireless communication. One non-limiting example of an implantable accelerometer is the Medtronic Reveal LINQ or catheter based accelerometers. Patient posture can also be used as a surrogate for fluid volume overload. A patient may be sleeping erect or semi-erect due to fluid in the lungs of the patient.

A fluid removal volume during a current cycle can be measured using a flow sensor and received into the computing device either automatically or manually entered into the computing device. The net fluid removal volume can be calculated from the difference between the volume of fluid infused into the patient and the volume of fluid removed from the patient. Additional examples include a temperature of effluent removed during the current cycle, and an effluent color and/or clarity of effluent removed during the current cycle. Temperature of the effluent can be detected using a temperature sensor in an effluent line of a cycler. The effluent color and clarity can be determined using a spectroscope. A sample of filtrate from the effluent line can be removed and analyzed using an off-line or integrated spectroscope to determine the color and clarity of the filtrate. Blood solute levels can be determined by an implantable sensor with ion selective electrodes. Alternatively, a blood assay can be completed and the information received by the system. Patient blood pressure, blood solute levels and other parameters may be determined with a wearable sensor. A wearable sensor can be included on a patch or other material in contact with the skin of the patient. The patch or material can be adhered or fixed onto the skin surface using methods known to those of skill in the art. The processor can automatically receive data from the wearable sensor.

In operation 108, the one or more parameters can be analyzed in view of one or more target values stored in a machine readable storage medium of the processor. Multiple instances of operation 108 are depicted in FIG. 1. For example, in operation 108a, the net or given fluid removal volume of the patient can be analyzed in view of a target fluid removal volume. The net fluid removal volume can be determined by the difference between a volume of fluid infused into the patient and the volume of fluid removed from the patient, as measured by flow sensors, however the flow sensors can be used to measure any volume of fluid removed. In operation 108b, a patient posture during the peritoneal dialysis session can be analyzed. In operation 108c, an effluent temperature of the removed peritoneal dialysate filtrate can be analyzed. In operation 108d, an effluent color and/or clarity can be analyzed in view of a target effluent color or clarity. Peritoneal dialysis lost dwell time is the amount of dialysis time that is lost during fluid exchanges between cycles. Lost dwell time can be caused by clogging of the dialysis catheter leading to reduced flow rate of peritoneal dialysate fluid into and out of the patient. The described system can monitor lost dwell time, and, if an unacceptable lost time is detected, could increase the glucose concentration and/or modify the ionic concentration in the next cycle to draw out more fluid from the patient or to make a larger electrolyte adjustment in a shorter time. Drawing out more fluid or making a larger electrolyte adjustment in a shorter time can allow the patient to achieve fluid removal and/or therapy targets even though dialysis time is reduced by poor catheter performance.

In operation 110, a determination is made whether an adjustment to the dialysis parameters is desired based on the analysis performed during operation 108. For example, if the net or given fluid removal volume is lower than the target fluid removal volume, a concentration of an osmotic agent, such as glucose (a dialysis parameter), can be increased in a subsequent cycle. Alternatively, dwell time could be decreased, and/or a number of subsequent cycles could be increased. Conversely, if the net or given fluid removal volume from the peritoneal cavity is higher than the target fluid removal volume, the osmotic agent concentration can be decreased in a subsequent cycle, dwell time could be increased, and/or a number of subsequent cycles could be decreased.

As another example, if the target patient posture is erect or supine, adjustments to cycle volume, dwell time, and/or composition (dialysis factors) can be desirable. As described, the patient posture can be analyzed, and changes in posture used to determine the degree of fluid overload in the patient. An osmotic agent concentration could be increased in the next cycle in order to remove additional fluid from the patient if the patient shows signs of fluid overload. An upright posture at night may indicate excess fluid and trigger a larger ultrafiltration goal, such as by increasing the osmotic agent concentration, decreasing dwell time, and/or increasing the number of cycles in the peritoneal dialysis session. Further, an upright posture can result in a smaller contact area of the peritoneum with the fluid, and the cycle volume increased to compensate. A longer dwell time and higher osmotic agent concentration can also compensate for the upright posture. If the effluent temperature is above a particular threshold, the patient may be experiencing an infection, and operation 110 can determine an adjustment to eliminate further cycles is necessitated. Additionally, the temperature of the peritoneal dialysate infused into the patient can be heated to within a predetermined range of the patient body temperature, as determined by the effluent temperature, for increased patient comfort. If an effluent color and/or clarity falls outside of a particular range of values, the patient may be experiencing an infection and/or experiencing a failing peritoneum. For example, growth of bacteria in the peritoneum, infiltration of white blood cells into the peritoneum in response to the infection, and the leakage of red blood cells could all be signs of infections and/or a failing peritoneum. The systems and methods of the invention can then alert the patient or clinician using an auditory or electronic display on a graphical user interface positioned on the dialysis machine. Alternatively, the alert can be stored in a processor and generated in a printed report for review by the patient or clinician. Alerts can also be delivered wireless to a connected device and/transmitted via the internet to an Electronic Health Record (EHR) for later use and action by a clinician.

One of ordinary skill in the art will recognize that the analysis of operation 108 can be performed in any number of ways. Rather than determining if the patient parameter meets a condition relative to a target, a determination can be made whether the patient parameter fails to meet a condition relative to a target. A determination can be made whether the target meets or fails to meet a condition relative to the patient parameter. Other variations are considered as equivalent approaches under the general concept of operation 108.

Any number or combination of patient parameters can be monitored and analyzed during a peritoneal dialysis session, and any number or combination of dialysis parameters can be adjusted for a subsequent cycle of the peritoneal dialysis session based on the analysis. Table 1 contains illustrative examples of patient parameters and dialysis parameters.

TABLE 1

| Patient Parameters | Dialysis Parameters |
|---|---|
| Patient blood pressure | Osmotic agent concentration |
| Volume of effluent removed | Osmotic agent concentration, dwell time, number of cycles |
| Patient goal | Dwell time, cycle volume, number of cycles, fluid removal volume |
| Blood solute level | Dwell time |
| Effluent solute level | Dwell time, Osmotic agent concentration, cycle volume, number of cycle |
| Effluent color/clarity | Number of cycles |
| Effluent temperature | Patient comfort goal |
| Patient posture | Cycle volume, dwell time, composition, osmotic agent concentration |
| Tidal volume remaining in a patient | Cycle volume |
| Intraperitoneal pressure | Cycle volume |

If in operation 110 of FIG. 1, a determination is made that an adjustment to the dialysis parameters is not desired, the method can proceed to operation 114. In operation 114, control signals implementing dialysis parameters (without adjustment) for a subsequent cycle can be transmitted to components of the system.

If in operation 110, a determination is made that an adjustment to the dialysis parameters is desired, the method can proceed to operation 112. In operation 112, an adjustment to the dialysis parameters can be determined based on the analysis performed during operation 108. Multiple instances of operation 112 are depicted in FIG. 1. For example, in the volume of effluent example, an adjustment to one or more of a dwell time for a subsequent cycle and a number of subsequent cycles can be determined in operation 112a. Alternatively, in the patient posture example, an adjustment to one or more of cycle volume, dwell time, and composition can be determined in operation 112b. Alternatively, in operation 112c, in the effluent temperature example, an adjustment ending further cycling can be determined in operation 112d in the case of infection and an alert issued to the patient or health care professional. Alternatively, the temperature of the peritoneal dialysate in the next cycle could be increased or decreased for increased patient comfort.

If in operation 112, a determination is made to end further cycling (as shown in operations 112c and 112d), the method 100 can proceed to operation 118 and end. However, if a determination is made to adjust dialysis parameters (as shown in operations 112a and 112b), the method 100 can proceed to operation 114.

In operation 114, control signals implementing dialysis parameters (with adjustment) for a subsequent cycle can be transmitted to components of the system and stored in a machine readable storage medium. After operation 114, the method 100 can proceed to operation 116. In operation 116, a determination is made whether the cycle initiated by the control signals sent in operation 114 is the last cycle of the peritoneal dialysis session. If in operation 116, a determination is made that the cycle initiated by the control signals sent in operation 114 is the last cycle, the method 100 can proceed to operation 118 and the method can end. If in operation 116, a determination is made that the cycle initiated by the control signals sent in operation 114 (the new cycle) is not the last cycle, then the method can return to operation 106, where one or more patient parameters can be received during the new cycle of the peritoneal dialysis session.

Figure 2:
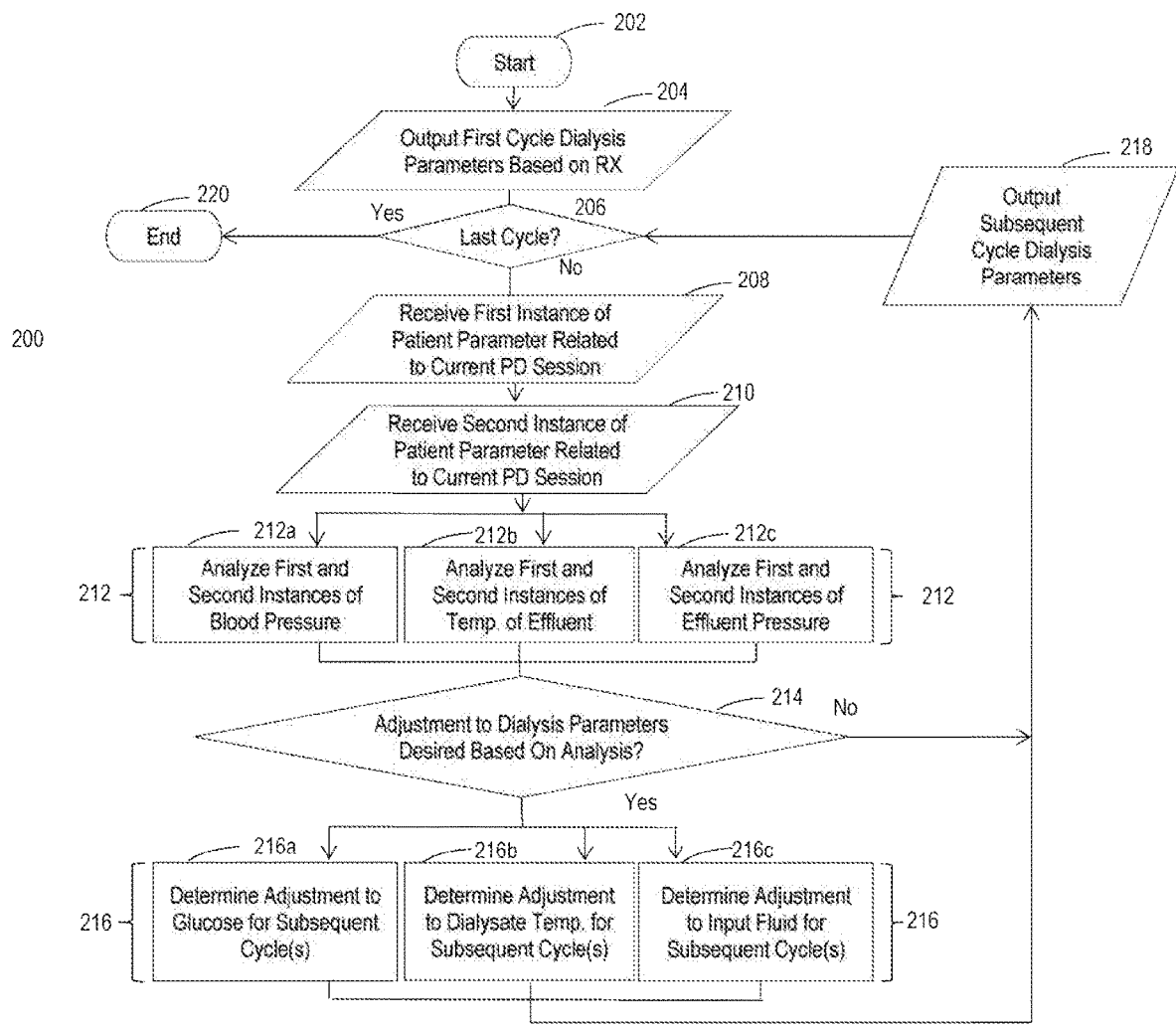
FIG. 2 shows a flow chart for a method of adjusting subsequent cycle dialysate parameters based on changes in patient parameters during a prior cycle.

FIG. 2 is a flowchart of a computer implemented method 200 for monitoring patient parameters during a peritoneal dialysis session to make intercycle adjustments to dialysis parameters for a subsequent cycle within the peritoneal dialysis session. The method can be performed using a system programmed or constructed to monitor patient parameters during cycles of a peritoneal dialysis session and to make modifications within the same peritoneal dialysis session. The system can include a machine readable storage medium including instructions that, when executed by a dialysis machine, cause the dialysis machine and related components to perform the any one of the methods of the present invention.

The method 200 can begin in operation 202, initiating a peritoneal dialysis session. One or more dialysis parameters making up a dialysate prescription can be received by the system and stored in a machine readable storage medium. In operation 204, control signals implementing dialysis parameters for a first cycle can be sent to components of the system based on a peritoneal dialysis prescription. For example, a processor of the system can be in communication with the concentrate source of the system and can control the movement of fluid from the concentrate source to a peritoneal dialysate generation flow path of the system based on the dialysis parameters for the first cycle of the peritoneal dialysis session.

In operation 206, a determination can be made whether the cycle initiated by the control signals (sent in operation 204) is the last cycle of the peritoneal dialysis session. If in operation 206, a determination is made that the cycle initiated by the control signals is the last cycle, the method 200 can proceed to operation 220 and the method 200 can end. If in operation 206, a determination is made that the cycle initiated by the control signals is not the last cycle, then the method can proceed to operation 208.

In operation 208, a first instance of a patient parameter can be received during or after the current cycle of the peritoneal dialysis session and stored in the machine readable storage medium. Patient parameters can be received as parameter input and/or from one or more sensors. For example, a first instance of a patient blood pressure can be received from an implantable or external blood pressure sensor, or alternatively the patient blood pressure can be manually input into the system. In operation 210, a second instance of a patient parameter can be received during or after the current cycle of the peritoneal dialysis session. For example, a second instance of a patient blood pressure can be received by the system.

In operation 212, the first and second instances of the patient parameter can be analyzed. Multiple instances of operation 212 are depicted in FIG. 2. For example, in operation 212*a*, first and second instances of blood pressure are analyzed to determine a trend. The system can adjust subsequent cycles based on the change in patient blood pressure. As another example, in operation 212*b*, first and second instances of effluent temperature can be analyzed to determine correlations to other parameters, such as dialysate temperature. As another example, in operation 212*c*, first and second instances of intraperitoneal pressure can be analyzed to determine a trend during a cycle.

In operation 214, a determination can be made whether an adjustment to the dialysis parameters is desired based on the analysis performed during operation 212. For example, a change in patient blood pressure that is decreasing or trending low during a cycle could indicate that fluid is being removed too quickly. If the change in patient blood pressure is greater than a predetermined threshold, the osmotic agent concentration could be reduced in a next cycle to modify the fluid removal rate and thereby maintain a more steady blood pressure.

As another example, if the temperature of effluent removed at the multiple instances shows a decrease below a threshold, a temperature of a dialysate temperature for a subsequent cycle can be increased. Alternatively, temperature of effluent removed at the multiple instances can be compared against performance data (such as UF Volume) and correlated versus temperature, allowing for fine tuning or optimization of temperature for patient comfort and/or performance.

As another example, first and second instances of intraperitoneal pressure can indicate peritoneum "fullness" to manage cycle volume. Intraperitoneal pressure can be measured by a pressure sensor in the infusion line, and can indicate incomplete removal of previous cycle volume, leaving a tidal volume remaining in the patient. Accordingly, a generated or regenerated fluid amount for a subsequent cycle can be adjusted to compensate for the incomplete removal, such as by reducing the cycle volume. In response to pressure changes, the dwell time and fill and empty rates can be adjusted by the system. If, due to decreased pressure and flow rate, the fill and empty time is increased, the dwell time can be automatically increased by the system to achieve equivalent therapy as with higher intraperitoneal pressure. Changes in intraperitoneal pressure over time within a session can be trended and recorded to monitor intraperitoneal pressure changes over time. Increases in pressure may be correlated with peritonitis and higher pressure is correlated with night enteric peritonitis which leads to higher mortality.

If in operation 214, a determination is made that an adjustment to the dialysis parameters is not desired, the method can proceed to operation 218. In operation 218, control signals implementing dialysis parameters (without adjustment) for a subsequent cycle can be transmitted to components of the system.

If in operation 214, a determination is made that an adjustment to the dialysis parameters is desired, the method can proceed to operation 216. In operation 216, an adjustment to the dialysis parameters can be determined based on the analysis performed during operation 212. Multiple instances of operation 216 are depicted in FIG. 2. For example, in the blood pressure example, an adjustment to an osmotic agent concentration can be determined in operation 216*a*. Alternatively, in the effluent temperature example, an adjustment to dialysate temperature can be determined in operation 216*b*. Alternatively, in operation 216*c*, in the pressure example, an adjustment to the amount of peritoneal dialysate infused into the patient can be determined. After operation 216, the operation can proceed to operation 218.

In operation 218, control signals implementing dialysis parameters (with adjustment) for a subsequent cycle can be transmitted to components of the system. After operation 218, the method 200 can proceed to operation 206. In operation 206, a determination is made whether the cycle initiated by the control signals (sent in operation 218) is the last cycle of the peritoneal dialysis session. If in operation 218, a determination is made that the cycle initiated by the control signals is the last cycle, the method 200 can proceed to operation 220 and the method can end. If in operation 206, a determination is made that the cycle initiated by the control signals (sent in operation 218, i.e., the new cycle) is not the last cycle, then the method can return to operation 208, where a first instance of a patient parameter can be received during or after the current cycle of the peritoneal dialysis session.

Additional parameters can be included, not shown in FIG. 2 for clarity. For example, a pH of the effluent can be determined. A lower effluent pH could be an early indicator of infection or failing peritoneum health. Changes to the pH during a dwell can be determined by removing small amounts of filtrate from the patient at multiple times during a cycle and analyzing the pH of the removed filtrate. The pH of the filtrate can be trended between cycles or sessions. The peritoneal dialysate generation system with an integrated cycler advantageously allows for the creation of neutral and sterile peritoneal dialysate due to the online sterilization. As such, changes in effluent pH during a cycle are easily determined. The dialysate pH can be adjusted as necessary by adding acid or base to the dialysate in response to the effluent pH using the dialysis machines of the present invention capable of adjusting the pH dynamically in response to instructions or inputs. Additionally, appropriate medical intervention can be taken in response to detection of infection by changes in the pH of the dialysate.

Removing small amounts of fluid at various times during a cycle also allows for a calculation of membrane transfer efficiency. For example, the second instance of the volume of fluid removed from the peritoneal cavity can be compared to the first instance of the volume of fluid removed from the peritoneal cavity to determine the membrane transfer efficiency. The membrane transfer efficiency is a function of the fluid removed from the patient in either a given cycle or a given session. Membrane transfer efficiency is also a function of the PD fluid dextrose, volume removed in a specific session, dwell time, cycle number, and other factors. One of skill in the art will understand that the factors in determining the membrane transfer efficiency can be determined using the systems and calculated. Membrane transfer efficiency can also be calculated based on the changes in effluent solute level in the peritoneal dialysate within the peritoneal cavity of a patient over time. The conductivity or the effluent solute level can be determined based on information from a conductivity sensor or ion selective electrode in the effluent line and the membrane transfer efficiency automatically calculated. Based on the calculated membrane transfer efficiency, the composition of the peritoneal dialysate can be adjusted for subsequent cycles by changing the osmotic agent concentration or solute concentration of one or more ions in the dialysate.

Removing small amounts of fluid at various times during a cycle also allows for optimization of the dwell time. A low osmotic agent concentration in the effluent could indicate that the current cycle should be ended and a new cycle begun. Similarly, a plateau in the conductivity or concentration of one or more solutes could indicate that the current cycle should be ended and a new cycle begun. Alternatively, the osmolality of the effluent can be used to determine the optimal dwell time. The net or given volume of fluid removed at the end of the optimal dwell time can be used to optimize the cycle volume, dialysate composition, and cycle time of subsequent cycles.

The system can also receive the intra-session history of the patient. The intra-session history includes the goals from prior cycles in a session and the actual performance, as well as the cycle parameters including dwell time, composition of the peritoneal dialysate, cycle volume and any other parameters. The intra-session history can be analyzed to determine whether goals from previous cycles have been met, and if not, adjustments made to subsequent cycles. For example, the target fluid volume removed from a patient can be analyzed in light of the expected or target fluid volume removed. If the previous cycle did not remove as much fluid as the target, later cycles can include a higher osmotic agent concentration, or a shorter dwell time with additional cycles. The system can also vary the cycle drain rate. A dialysis session may be more time and therapy efficient to leave some volume in the peritoneal cavity of the patient during the first cycles by not decreasing the drain volume in early cycles and only fully removing all dialysate during the last cycle. The total cycle time is the dwell time, or therapy time, plus the time to fill and empty the peritoneal cavity of the patient. By decreasing the drain volume to leave some volume of peritoneal dialysate in the patient, the fill and empty time can be decreased, thereby increasing the dwell or therapy time. The fill and empty time can vary depending on the cycle volume and the flow rate into and out of the peritoneal cavity of the patient. Typically, the fill rate and drain rate is between 100 and 300 mL/min. The fill rate and drain rate can be adjusted to provide increased therapy time. Conversely, one could leave volume in during the last cycle as is commonly employed in tidal peritoneal dialysis. The composition of each of the cycles could be adjusted accordingly to maintain desired tonicity for good ultrafiltration clearance. The composition could be adjusted on the fly based on measured effluent volume and estimated tidal volume remaining in patient. The fill volume for a subsequent cycle can also be adjusted based on the tidal volume remaining in the patient.

The cycle volume, or amount of peritoneal dialysate infused into the patient, can be expected to be between 0.5 and 3 L per cycle. Typically for an adult, the cycle volume is about 1.5 L. When varying the cycle volume for therapeutic effect, the volume range can be varied by any amount, including by 0.1 L to 1 L. Varying the cycle volume could be done in small or large steps depending on how far from therapeutic target, as determined by the methods. Any cycle volume can be used, however in a preferred embodiment the upper limit of cycle volume is approximately 3.5 to 4 L.

Figure 3:
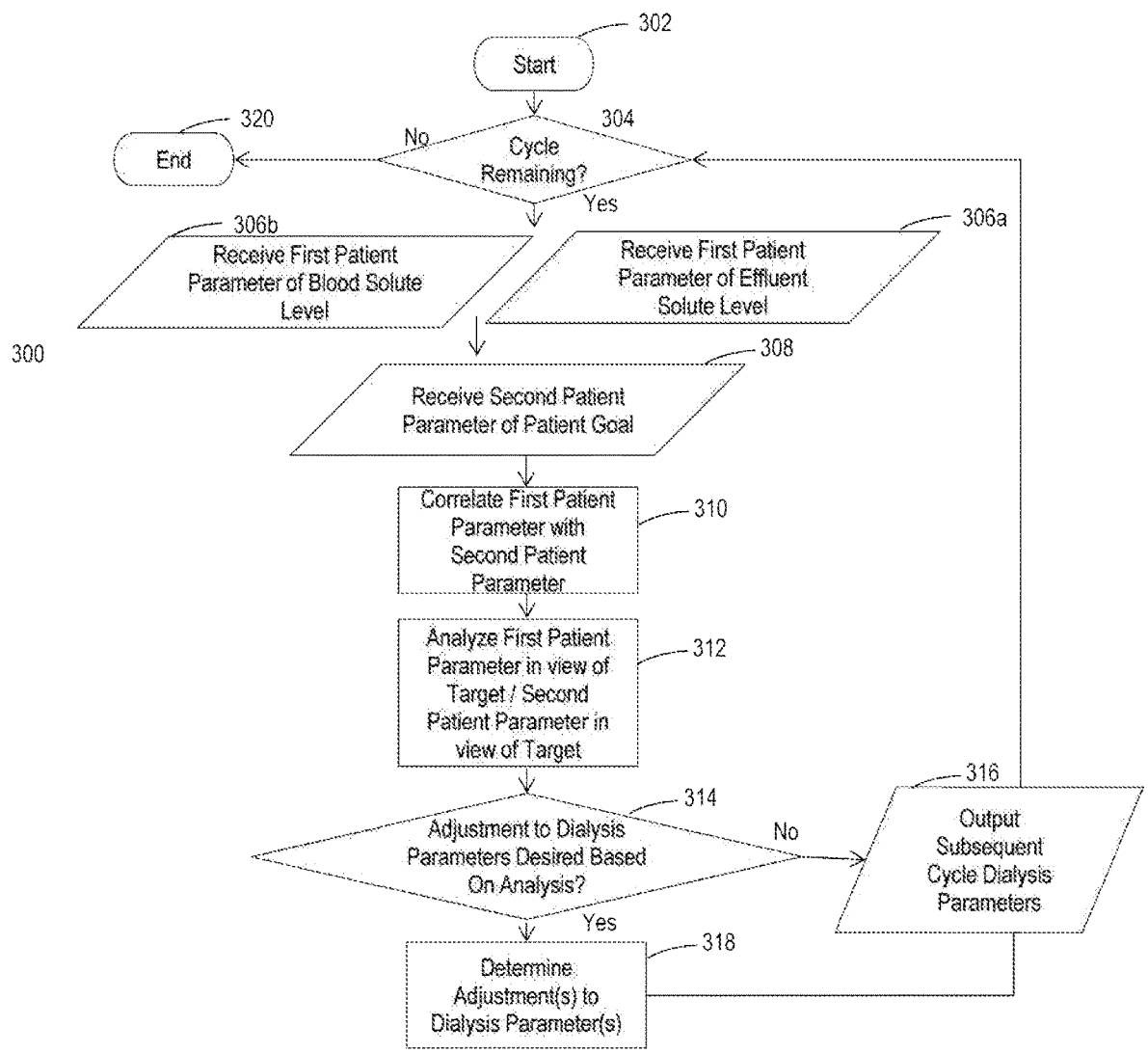
FIG. 3 shows a flow chart for a method of adjusting subsequent cycle dialysate parameters based on a correlation between patient or system parameters and target values.

FIG. 3 is a flowchart of a computer implemented method 300 for monitoring patient parameters during a peritoneal dialysis session to make intercycle adjustments to dialysis parameters for a subsequent cycle within the peritoneal dialysis session. The method 300 can enable a variable dwell time, and/or a variable cycle drain. The method can be performed using a system programmed or constructed to monitor patient parameters during a peritoneal dialysis session and to make intercycle modifications within the same peritoneal dialysis session. The system can include a machine readable storage medium including instructions that, when executed by a dialysis machine, cause the dialysis machine and related components to perform the described methods.

The method 300 can begin in operation 302. A peritoneal dialysis session can already be underway. In operation 304, a determination is made whether one or more cycles remain in the current peritoneal dialysis session after the current cycle that is already underway. If in operation 304, a determination is made that no more cycles remain, the method 300 can proceed to operation 320 and the method can end. If in operation 304, a determination is made that one or more cycles after the current cycle remain in the current peritoneal dialysis session, then the method 300 can proceed to operation 306.

In operation 306, a first patient parameter can be received related to the current cycle of the peritoneal dialysis session and stored in a machine readable storage medium. Patient parameters can be received as parameter input and/or from the one or more implantable or external sensors, or manually input into the system. One or more sensors can also be included in the peritoneal dialysis cycler. For example, in operation 306a an effluent solute level can be used to determine the amount of a solute removed from the patient, such as potassium, during the cycle can be received from a sensor along an effluent line of the system. Alternatively, in operation 306b, a blood solute level can be determined from an implantable or wearable sensor and received into the system.

In operation 308, a second and different patient parameter can be received related to the current cycle of the peritoneal dialysis session. For example, a patient goal can be entered as parameter input. An example of a patient goal would be the expected dialysis schedule or the number of cycles desired in a given peritoneal dialysis session. A patient may wish to include fewer cycles on certain days to provide greater flexibility in treatment. The number of cycles in a given session can be increased, or the net or given volume of fluid removed increased by increasing an osmotic agent concentration during a particular cycle to provide greater flexibility in later cycles or sessions. The patient goals may also include the amount of time available for therapy, desired volume removal, how the patient feels, physical activity planned/performed, and diet. For example, if the patient's expected dialysis schedule includes less therapy later in a week, the fluid removal can be more aggressive early in the week, allowing less therapy later in the week. A tired patient may be indicative of ineffective treatment, and the dialysate composition adjusted accordingly. If the patient goal includes an expected diet that is a high salt diet, or a high expected fluid intake, the dialysate osmotic agent concentration can be increased, or other adjustments made.

Due to the concentrations of potassium, sodium, the fluid level, or any other factors, certain patients may respond better with a greater number of short cycles than a lower number of long cycles, such as with five short cycles rather than four longer cycles or any other variety of cycles. The system can automatically adjust the dwell time and number of cycles in light of the sensed patient parameters to optimize therapy.

In operation 310, the first patient parameter can be correlated with the second patient parameter. For example, the amount of potassium removed during the cycle can be determined and the peritoneal dialysis prescription for the next cycle adjusted. Alternatively blood solute levels of potassium or other solutes can be determined. Solutes such as potassium, as well as water, have a higher removal rate early in a cycle dwell. Sodium is more effectively removed later in the dwell. By adjusting dwell time, the removal of potassium, sodium and water from the patient can be adjusted. For example, by increasing the dwell time, more sodium can be removed. Alternatively, by using additional cycles of shorter dwell times, more potassium and water can be removed from the patient. By determining the patient potassium, sodium, and fluid level, the system can automatically adjust the dwell time to optimize removal of each element from the patient. The amount of calcium and magnesium removed from the patient can also be used to adjust the dialysate prescription in the same manner. Because calcium and magnesium are generally included in the peritoneal dialysate, the concentration of calcium and magnesium could also be adjusted in the peritoneal dialysate to optimize removal using the dialysis machine of the present invention capable of adjusting the calcium and magnesium concentrations.

In operation 312, the first patient parameter can be analyzed in view of a first parameter target, and the second patient parameter can be analyzed in view of a second parameter target. For example, the amount of potassium removed during the current cycle can be analyzed in view of a target amount of potassium removed. The patient goal of fewer cycles per session (e.g., 2-3 cycles total session cycles) can be analyzed in view of the number of cycles remaining (e.g., 1-5) cycles after the current cycle.

In operation 314, a determination is made regarding whether an adjustment to the dialysis parameters is desired based on the analysis performed during operation 312. For example, if the level of potassium removed during the current cycle is within a target range of potassium to be removed, but the patient goal of fewer cycles per session is lower than the number of cycles remaining, then the system can determine that a reduction in the number of cycles remaining is acceptable.

If in operation 314, a determination is made that an adjustment to the dialysis parameters is not desired, the method can proceed to operation 316. In operation 316, control signals implementing dialysis parameters (without adjustment) for a subsequent cycle can be transmitted to components of the system.

If in operation 314 a determination is made that an adjustment to the dialysis parameters is desired, the method can proceed to operation 318. In operation 318, an adjustment to the dialysis parameters can be determined based on the analysis performed during operation 312. In the potassium and number of cycles example, because potassium removed during the current cycle is within a target range of potassium to be removed, but the patient goal of fewer cycles per session is lower than the number of cycles remaining, then an adjustment to the dialysis parameter number of cycles remaining can be made to remove one or more cycles of the session. After operation 318, the method 300 can proceed to operation 316, where control signals implementing dialysis parameters (with adjustment) can be transmitted to components of the system.

After operation 316, the method 300 can return to operation 304, where a determination is made whether one or more cycles remain in the current peritoneal dialysis session after the current cycle that is already underway.

In each of the methods illustrated in FIGS. 1-3, the system monitors parameters between or during a peritoneal dialysis cycle and makes modifications cycle-to-cycle within a session to optimize therapy.

Peritoneal Dialysate Generation and Integrated Cycler

Figure 4:
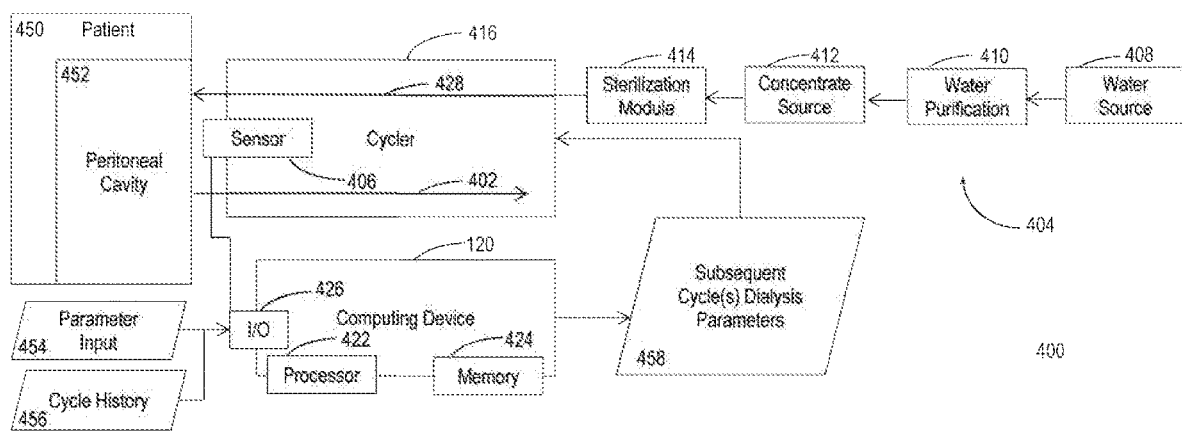
FIG. 4 shows a peritoneal dialysate generation system with an integrated cycler.

FIG. 4 shows a system 400 for monitoring patient parameters during a peritoneal dialysis session to make modifications within the same peritoneal dialysis session. One or more patient parameters can be obtained by the system 400 during the peritoneal dialysis session such as before, during, or after a cycle. The one or more patient parameters can be analyzed. One or more dialysis parameters can be adjusted for a subsequent cycle of the same peritoneal dialysis session based on the analysis.

The system 400 can include a peritoneal dialysate effluent line 402, a peritoneal dialysate generation flow path 404, one or more sensors 406 positioned in one or both of the peritoneal dialysate effluent line 402 and the peritoneal dialysate generation flow path 404, and a computing device 420. One of skill in the art will understand that one or more implantable sensors in the patient can be included, such as an implantable accelerometer or blood pressure monitor. The peritoneal dialysate effluent line 402 can be fluidly connected to a waste reservoir (not shown) to collect effluent.

The peritoneal dialysate generation flow path 404 can include a water source 408, one or more water purification modules 410, a concentrate source 412, a sterilization module 414, and an integrated cycler 416. The concentrate source 412 can contain one or more solutes. The water source 408, water purification module 410, concentrate source 412, sterilization module 414, and integrated cycler 416 can be fluidly connectable to the peritoneal dialysate generation flow path 404. The integrated cycler 416 can include the effluent line 402, an infusion line 428, and one or more pumps for infusing peritoneal dialysate into the peritoneal cavity 452 of the patient 450 and removing fluid from the peritoneal cavity 452 of the patient 450. Although drawn as separate infusion and effluent lines in FIG. 4, the system can use a combined effluent and infusion line. A single channel to the catheter can be used for removal and infusion of fluid, with the cycler diverting fluid as necessary. One or more processors 422 can adjust dialysis parameters for a current or subsequent cycle of the peritoneal dialysis session. For example, the processor 422 can adjust the movement of fluid from the concentrate source 412 to the peritoneal dialysate generation flow path 404 based on the monitored patient parameters.

The water source 408 can be a non-purified water source, such as tap water, wherein the water from the water source 408 can be purified by the system. A non-purified water source can provide water without additional purification, such as tap water from a municipal water source, water that has undergone some level of purification, but does not meet the definition of "purified water" provided, such as bottled water or filtered water. The water source can contain water meeting the WHO drinkable water standards provided in *Guidelines for Drinking Water Quality*, World Health Organization, Geneva, Switzerland, 4th edition, 2011. Alternatively, the water source 408 can be a source of purified water, meaning water that meets the applicable standards for use in peritoneal dialysis without additional purification. The system pumps water from the water source to the water purification module 410 to remove chemical contaminants in the fluid in preparation of the dialysate. The water purification module 410 can contain a combination of chemical absorbants, such and activated carbon or other compounds known in the art The sorbent may also contain one ore more ion exchange materials that remove ionic species from the water in exchange for $H^+$ or $OH^-$ ions.

The system can pump the fluid to a sterilization module 414 for sterilization of the peritoneal dialysate prior to infusion into the patient. The sterilization module 414 can include one or more of a first ultrafilter, a second ultrafilter, and a UV light source, or any combination thereof. The sterilization module can be any component or set of components capable of sterilizing the peritoneal dialysate.

The concentrate sources 412 can contain one or more solutes for generation of the peritoneal dialysate from purified water. The concentrates in the concentrate source 412 are utilized to create a peritoneal dialysis fluid that matches a dialysis prescription. A concentrate pump (not shown) in communication with the processor or computing unit controls the movement of concentrates from the concentrate sources 412 into the peritoneal dialysate generation flow path 404. Table 2 provides non-limiting exemplary ranges of commonly used components of peritoneal dialysate. One of skill in the art will understand that alternatives to the components listed in Table 2 can be used. Other osmotic agents can be used in addition to, or in place of, the dextrose, including icodextrin or amino acid solutions, including dialysate with multiple osmotic agents. Although the sources of sodium, calcium, and magnesium listed in Table 2 are chloride salts, other sodium, magnesium, and calcium salts can be used, such as lactate or acetate salts. Peritoneal dialysate may also contain buffers for maintaining pH of the peritoneal dialysate. Exemplary, non-limiting examples of suitable buffers include bicarbonate buffer, acetate buffer or lactate buffer. Although not generally used in peritoneal dialysis, potassium chloride can be used for hypokalemic patients who don't receive sufficient potassium through diet. The concentrate sources 412 can include any number of concentrates combined or in separate concentrate sources. For example, one or more osmotic agent sources can be included in addition to a single ion concentrate source. Alternatively, multiple ion concentrate sources can be used with each ion concentrate in a separate concentrate source. Any combination of concentrates in any number of concentrate sources can be used with the invention.

TABLE 2

| Component | Concentration |
| --- | --- |
| Sodium chloride | 132-134 mmol/L |
| Calcium chloride dehydrate | 1.25-1.75 mmol/L |
| Magnesium chloride hexahydrate | 0.25-0.75 mmol/L |
| Sodium Lactate | 35-40 mmol/L |
| Dextrose (D-glucose) monohydrate | 0.55-4.25 g/dL |
| pH | 5-6 |
| Osmolality | 346-485 (hypertonic) |

The water source 408, water purification module 410, concentrate source 412, and sterilization module 414 can be fluidly connectable to the integrated cycler 416 for immediate delivery of the generated peritoneal dialysate to the patient. Alternatively, a peritoneal dialysate reservoir (not shown) can be included to collect the generated peritoneal dialysate for later use. One or more processors 422 which can be part of a larger computing device 420, can control the movement of fluid from the concentrate source 412 to the peritoneal dialysate generation flow path 434 based on a peritoneal dialysate prescription 430. The processors 422 can also control the pumps in the cycler and a heater (not shown) for heating the peritoneal dialysate prior to infusion. One or more sensors can be included in the peritoneal dialysate generation flow path 404 and/or the infusion line 428 to ensure the therapy delivered to the patient matches the peritoneal dialysate prescription. The concentrate sources can infuse each particular concentrate to provide an infused ion concentration that is lower than a prescribed amount for a particular patient. One desired outcome to be provide a concentration for a particular ion that is lower than a patient's pre-dialysis ion concentration. Additionally, if multiple ion sources are to be delivered by a concentrate source, the present system can selectively dilute a desired ion while maintaining concentration levels for other ions.

Hence, the present invention can avoid adjusting down every ion insofar as an added diluent may adversely affect concentrations of ions already in a normal range.

Patient parameters can be derived from fluid sampled by one or more sensors 406 when removed or from or introduced into the peritoneal cavity 452 of the patient 450. Patient parameters can also be derived from the patient 450 such as by monitoring blood pressure via a sensor 406 monitoring the patient 450. Patient parameters can also be input into the system 400 as a parameter input 454. A sensor 406 can be positioned in the peritoneal dialysate effluent line 402, the peritoneal dialysate generation flow path 404, or in both the peritoneal dialysate effluent line 402 and the peritoneal dialysate generation flow path 404. A sensor 406 can be connected to the patient 450. For example, a blood pressure sensor can be connected to the patient 450. Patient parameters can be derived using the one or more or more sensors 406. Implantable sensors, such as implantable cardiac rhythm management systems or other sensors can be in communication with the processors 422 to provide the system with patient parameters. The sensors 406 can be separate sensors, a combined sensor positioned along both the peritoneal dialysate effluent line 402 and the peritoneal dialysate generation flow path 404, or combined or separate sensors along a common peritoneal dialysate effluent line and peritoneal dialysate generation flow path. The sensors 406 can be placed at various locations along the peritoneal dialysate effluent line 402 and the peritoneal dialysate generation flow path 404, including within or between the cycler 416, the water source 408, the water purification module 410, the concentrate source 412, and the sterilization module 414, or between the cycler 416 and the peritoneal cavity 452. The sensors 406 can be posited to take measurements directly from the patient 450.

The one or more sensors 406 can include blood pressure sensor to measure blood pressure of a patient 450 during a cycle. The sensor 406 can include a flow sensor to measure a volume of fluid removed from a peritoneal cavity 452 of the patient 450. The sensor 406 can include a solute concentration sensor to measure a solute concentration of the fluid removed from the patient. The sensor 406 can include a refractive index sensor to measure glucose or other osmotic agent concentration in the fluid removed from the patient. The sensor 406 can include a conductivity sensor or ion selective electrodes to measure conductivity or solute concentration of the fluid removed from the patient. The sensor 406 can include a pressure sensor to measure a pressure of fluid removed from a patient. The sensor 406 can include a temperature sensor to measure a temperature of fluid removed from a patient.

The computing device 420 can include the one or more processors 422, memory 424, and one or more input/output interfaces 426. The memory 424 can be in communication with the processor 422 and store instructions that when executed perform methods. The input/output interfaces 426 can include an input interface to receive parameter input 454, an input interface to receive intra-session cycle history 456 of the patient, an input port to receive information from the one or more sensors 406, and an output port to output control signals implementing dialysis parameters (with or without adjustment) for a subsequent cycle. The processor 422 can be in communication with the at least one sensor 406. As with all features of the present application, intervening components (such as the input/output interface 426) can be present between the processor 422 and the sensor 406. The computing device 420 can be a stand-alone device independent of the integrated cycler 416, or can be a part of the integrated cycler 416. The computing device 420 can be a remote device in network communication with the sensor 406, such as via the Internet.

An alternative system for monitoring patient parameters during a peritoneal dialysis session to make modifications within the peritoneal dialysis session can include a peritoneal dialysate regeneration module, a pump, and an infusion line. The infusion line can be fluidly connected to the peritoneal dialysate generation flow path 404 downstream of the sterilization module 414. The peritoneal dialysate effluent line 402 can be fluidly connected to the peritoneal dialysate generation flow path 404 upstream of the peritoneal dialysate regeneration module. The peritoneal dialysate regeneration module can include a sorbent cartridge, an electrodialysis unit, one or more ultrafilters, or any other combination of components for removal of contaminants from the dialysate removed from the patient. The used peritoneal dialysate, after regeneration, can be pumped back into the peritoneal dialysate generation flow path 404 for reuse.

One skilled in the art will understand that various combinations and/or modifications and variations can be made in the systems and methods depending upon the specific needs for operation. Features illustrated or described as being part of an aspect of the invention may be used in the aspect of the invention, either alone or in combination.

We claim:

1. A computer implemented method of adjusting intercycle patient parameters during peritoneal dialysis, performed by a system having one or more processors programmed to perform:

receiving, by the one or more processors of the system, one or more patient parameters during a single peritoneal dialysis session from a sensor;

receiving, by the one or more processors of the system, one or more dialysis parameters used during the peritoneal dialysis session;

storing the one or more patient parameters and one or more dialysis parameters in a machine-readable storage medium for storing instructions adjusting one or more dialysis parameters for a subsequent cycle of the single peritoneal dialysis session based on the patient parameters and dialysis parameters; wherein the step of adjusting one or more dialysis parameters is carried out by at least one of the one or more processors of the system in communication with a peritoneal dialysate generation flow path;

wherein at least one or more of:

a) the method further comprises receiving a target fluid removal volume by the one or more processors of the system comparing a volume of effluent removed to the target fluid removal volume by the one or more processors of the system; and wherein the step of adjusting one or more dialysis parameters for the subsequent cycle comprises the step of adjusting a dwell time, a number of cycles, or combinations thereof;

b) the method further comprises the steps of determining a change in patient blood pressure during the peritoneal dialysis cycle by the one or more processors of the system; and decreasing a dialysate osmotic agent concentration in a subsequent cycle if the change in patient blood pressure exceeds a predetermined threshold;

c) wherein the one or more patient parameters include a patient goal; wherein the patient goal is any one of an expected fluid intake, an expected diet, an expected dialysis schedule, and combinations thereof; and wherein the step of adjusting one or more dialysis parameters for the subsequent cycle of the single peritoneal dialysis session comprises increasing the osmotic agent concentration in response to a high expected fluid intake, a high salt diet, an expected dialysis schedule of fewer dialysis sessions, and combinations thereof; and/or d) the step of adjusting the one or more dialysis parameters for the subsequent cycle comprises increasing (a) the dwell time, (b) the osmotic agent concentration, or (c) combinations thereof, if a patient posture is determined to be erect.

2. The method of claim 1, wherein the one or more patient parameters include any one of:
   i) the patient blood pressure;
   ii) the fluid removal volume;
   iii) the patient goal;
   iv) a blood solute level;
   v) an effluent solute level;
   vi) an effluent temperature;
   vii) an effluent color or clarity;
   viii) the patient posture;
   ix) a tidal volume remaining in patient;
   x) an intraperitoneal pressure; and
   xi) combinations thereof.

3. The method of claim 2, further comprising the step of adjusting a temperature of peritoneal dialysate for a subsequent session to be within a predetermined range of the effluent temperature.

4. The method of claim 1, wherein the step of adjusting one or more dialysis parameters comprises adjusting any one of:
   i) the number of cycles;
   ii) the dwell time;
   iii) a dialysate temperature;
   iv) a fill volume;
   v) a dialysate pH;
   vi) the dialysate osmotic agent concentration;
   vii) a fluid removal volume;
   viii) a drain volume;
   ix) a fill rate;
   x) a drain rate; and
   xi) combinations thereof.

5. The method of claim 1, wherein the step of receiving one or more patient parameters during the single peritoneal dialysis session comprises sampling a peritoneal dialysate effluent.

6. The method of claim 1, wherein at least one of the one or more patient parameters is obtained from a sensor positioned in an integrated cycler.

7. The method of claim 1, wherein at least one of the one or more patient parameters is obtained from an implantable or wearable sensor.

8. The method of claim 1, further comprising the steps of:
   receiving a target fluid removal volume by the one or more processors of the system;
   comparing a volume of effluent removed to the target fluid removal volume by the one or more processors of the system; and
   wherein the step of adjusting one or more dialysis parameters for the subsequent cycle comprises the step of adjusting a dialysate osmotic agent concentration.

9. The method of claim 8, wherein the step of adjusting the dialysate osmotic agent concentration comprises increasing an osmotic agent concentration if the target fluid removal volume is higher than the volume of effluent removed; and decreasing the osmotic agent concentration if the target fluid removal volume is lower than the volume of effluent removed.

10. The method of claim 1, further comprising the steps of:
    receiving the target fluid removal volume by the one or more processors of the system;
    comparing the volume of effluent removed to the target fluid removal volume by the one or more processors of the system; and
    wherein the step of adjusting one or more dialysis parameters for the subsequent cycle comprises the step of adjusting the dwell time, the number of cycles, or combinations thereof.

11. The method of claim 1, comprising the steps of determining the change in patient blood pressure during the peritoneal dialysis cycle by the one or more processors of the system; and decreasing the dialysate osmotic agent concentration in the subsequent cycle if the change in patient blood pressure exceeds the predetermined threshold.

12. The method of claim 1, wherein the one or more patient parameters include a patient goal; wherein the patient goal is any one of an expected fluid intake, an expected diet, an expected dialysis schedule, and combinations thereof; and
    wherein the step of adjusting one or more dialysis parameters for the subsequent cycle of the single peritoneal dialysis session comprises increasing an osmotic agent concentration in response to a high expected fluid intake, a high salt diet, an expected dialysis schedule of fewer dialysis sessions, and combinations thereof.

13. The method of claim 1, wherein the step of adjusting the one or more dialysis parameters for the subsequent cycle comprises increasing (a) a dwell time, (b) an osmotic agent concentration, or (c) combinations thereof, if a patient posture is determined to be erect.

14. The method of claim 1, further comprising the step of obtaining an intra-session history for a patient by the one or more processors of the system; and wherein the one or more dialysis session parameters are adjusted based on the intra-session history for the patient.

15. The method of claim 1, the system comprises:
    the peritoneal dialysate generation flow path having
    i) a water source fluidly connectable to the peritoneal dialysate generation flow path;
    ii) one or more water purification modules fluidly connectable to the peritoneal dialysate generation flow path;
    iii) one or more concentrate sources fluidly connectable to the peritoneal dialysate generation flow path; the concentrate source containing one or more solutes and including at least an osmotic agent source and an ion concentrate source;
    iv) at least one concentrate pump; the concentrate pump controlling the movement of fluid from the concentrate sources to the peritoneal dialysate generation flow path;
    v) a sterilization module fluidly connectable to the peritoneal dialysate generation flow path;
    an integrated cycler fluidly connected to the peritoneal dialysate generation flow path; the integrated cycler having at least an infusion line and an effluent line or a combined infusion and effluent line; and
    the one or more processors further programmed to determine a peritoneal dialysate prescription and control the at least one concentrate pump and integrated cycler based on the peritoneal dialysate prescription.

16. The method of claim 15, the one or more processors comprising one or more input/output interfaces for receiving the one or more patient parameters.

17. The method of claim 15, further comprising a peritoneal dialysate regeneration module fluidly connected to the effluent line or combined infusion and effluent line and the peritoneal dialysate generation flow path.

18. The method of claim 15, wherein at least one sensor is positioned in the effluent line or combined infusion and effluent line and in communication with the processor.

19. The method of claim 18, the sensor sensing any one of:
   i) a temperature of a fluid in the effluent line or combined infusion and effluent line;
   ii) a conductivity of the fluid in the effluent line or combined infusion and effluent line;
   iii) a solute concentration of the fluid in the effluent line or combined infusion and effluent line; or
   iv) combinations thereof.

* * * * *